United States Patent
Senechal et al.

(10) Patent No.: US 10,108,852 B2
(45) Date of Patent: Oct. 23, 2018

(54) FACIAL ANALYSIS TO DETECT ASYMMETRIC EXPRESSIONS

(71) Applicant: Affectiva, Inc., Waltham, MA (US)

(72) Inventors: Thibaud Senechal, Cambridge, MA (US); Rana el Kaliouby, Boston, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 14/031,907

(22) Filed: Sep. 19, 2013

(65) Prior Publication Data
US 2014/0016860 A1    Jan. 16, 2014

Related U.S. Application Data

(63) Continuation-in-part of application No. 13/153,745, filed on Jun. 6, 2011.
(Continued)

(51) Int. Cl.
*G06K 9/00* (2006.01)
*A61B 5/16* (2006.01)
(Continued)

(52) U.S. Cl.
CPC .......... *G06K 9/00302* (2013.01); *A61B 5/165* (2013.01); *G06F 19/3418* (2013.01);
(Continued)

(58) Field of Classification Search
CPC ............ A61B 5/02055; A61B 5/02405; A61B 5/0533; A61B 5/08; A61B 5/11;
(Continued)

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Vincent Rudolph
*Assistant Examiner* — Shaghayegh Azima
(74) *Attorney, Agent, or Firm* — Adams Intellex, PLC (57) ABSTRACT

A system and method for facial analysis to detect asymmetric expressions is disclosed. A series of facial images is collected, and an image from the series of images is evaluated with a classifier. The image is then flipped to create a flipped image. Then, the flipped image is evaluated with the classifier. The results of the evaluation of original image and the flipped image are compared. Asymmetric features such as a wink, a raised eyebrow, a smirk, or a wince are identified. These asymmetric features are associated with mental states such as skepticism, contempt, condescension, repugnance, disgust, disbelief, cynicism, pessimism, doubt, suspicion, and distrust.

35 Claims, 6 Drawing Sheets

Related U.S. Application Data (60) Provisional application No. 61/703,756, filed on Sep. 20, 2012, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011.

(51) Int. Cl.
| | |
|---|---|
| *G06F 19/00* | (2018.01) |
| *G06Q 30/02* | (2012.01) |
| *A61B 5/0205* | (2006.01) |
| *A61B 5/024* | (2006.01) |
| *A61B 5/053* | (2006.01) |
| *A61B 5/08* | (2006.01) |
| *A61B 5/11* | (2006.01) |

(52) U.S. Cl.
CPC ..... *G06F 19/3481* (2013.01); *G06K 9/00315* (2013.01); *G06Q 30/0242* (2013.01); *A61B 5/02055* (2013.01); *A61B 5/02405* (2013.01); *A61B 5/0533* (2013.01); *A61B 5/08* (2013.01); *A61B 5/11* (2013.01)

(58) Field of Classification Search
CPC . A61B 5/165; G06F 19/3418; G06F 19/3481; G06K 9/00302; G06K 9/00315; G06Q 30/0242
USPC ......................................... 382/103, 224, 159
See application file for complete search history.

(56) References Cited

U.S. PATENT DOCUMENTS

| | | | |
|---|---|---|---|
| 3,870,034 A | 3/1975 | James | |
| 4,353,375 A | 10/1982 | Colburn et al. | |
| 4,448,203 A | 5/1984 | Williamson et al. | |
| 4,794,533 A | 12/1988 | Cohen | |
| 4,807,642 A | 2/1989 | Brown | |
| 4,817,628 A | 4/1989 | Zealear et al. | |
| 4,950,069 A | 8/1990 | Hutchinson | |
| 4,964,411 A | 10/1990 | Johnson et al. | |
| 5,008,946 A * | 4/1991 | Ando ................ | B60H 1/00757 180/167 |
| 5,016,282 A | 5/1991 | Tomono et al. | |
| 5,031,228 A | 7/1991 | Lu | |
| 5,219,322 A | 6/1993 | Weathers | |
| 5,247,938 A | 9/1993 | Silverstein et al. | |
| 5,259,390 A | 11/1993 | Maclean | |
| 5,507,291 A | 4/1996 | Stirbl et al. | |
| 5,572,596 A * | 11/1996 | Wildes ..................... | G06K 9/00 382/117 |
| 5,619,571 A | 4/1997 | Sandstorm et al. | |
| 5,647,834 A | 7/1997 | Ron | |
| 5,649,061 A | 7/1997 | Smyth | |
| 5,663,900 A | 9/1997 | Bhandari et al. | |
| 5,666,215 A | 9/1997 | Fredlund et al. | |
| 5,725,472 A | 3/1998 | Weathers | |
| 5,741,217 A | 4/1998 | Gero | |
| 5,760,917 A | 6/1998 | Sheridan | |
| 5,762,611 A | 6/1998 | Lewis et al. | |
| 5,772,508 A * | 6/1998 | Sugita ..................... | A63F 13/06 463/23 |
| 5,772,591 A | 6/1998 | Cram | |
| 5,774,591 A | 6/1998 | Black et al. | |
| 5,802,220 A | 9/1998 | Black et al. | |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,606,102 B1 | 8/2003 | Odom | |
| 6,629,104 B1 | 9/2003 | Parulski et al. | |
| 6,792,458 B1 | 9/2004 | Muret et al. | |
| 6,847,376 B2 | 1/2005 | Engeldrum et al. | |
| 7,003,135 B2 * | 2/2006 | Hsieh ................ | G06K 9/00228 382/103 |
| 7,013,478 B1 | 3/2006 | Hendricks et al. | |
| 7,058,209 B2 * | 6/2006 | Chen ................ | G06K 9/00281 382/117 |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,319,779 B1 * | 1/2008 | Mummareddy ... | G06K 9/00288 382/118 |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,593,551 B2 * | 9/2009 | Kamei ............... | G06K 9/00268 382/118 |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,747,801 B2 | 6/2010 | Han et al. | |
| 7,757,171 B1 * | 7/2010 | Wong ................ | G11B 27/105 345/156 |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1 | 4/2011 | Sharma | |
| 8,010,458 B2 | 8/2011 | Galbreath et al. | |

(56) References Cited

U.S. PATENT DOCUMENTS

| | | | |
|---|---|---|---|
| 8,189,866 B1* | 5/2012 | Gu | G06K 9/00335 348/169 |
| 8,401,248 B1* | 3/2013 | Moon | G06Q 30/0242 382/103 |
| 8,416,988 B2* | 4/2013 | Matsumoto | G06K 9/6253 340/506 |
| 8,437,573 B1* | 5/2013 | Agarwala | G06K 9/6292 382/283 |
| 8,515,184 B1* | 8/2013 | Medasani | G06K 9/6257 382/181 |
| 8,640,021 B2 | 1/2014 | Perez et al. | |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1* | 11/2002 | Eshelman | G06Q 50/22 340/573.1 |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0078513 A1 | 4/2003 | Marshall | |
| 2003/0093784 A1 | 5/2003 | Dimitrova et al. | |
| 2003/0191682 A1 | 10/2003 | Shepard et al. | |
| 2003/0191816 A1 | 10/2003 | Landress et al. | |
| 2004/0181145 A1* | 9/2004 | Al Bandar | A61B 5/164 600/408 |
| 2004/0181457 A1 | 9/2004 | Biebesheimer et al. | |
| 2004/0197013 A1* | 10/2004 | Kamei | G06K 9/00268 382/118 |
| 2005/0162511 A1* | 7/2005 | Jackson | G06T 15/02 348/61 |
| 2005/0283055 A1 | 12/2005 | Shirai et al. | |
| 2005/0289582 A1 | 12/2005 | Tavares et al. | |
| 2006/0019224 A1 | 1/2006 | Behar et al. | |
| 2006/0115157 A1* | 6/2006 | Mori | G06K 9/00221 382/190 |
| 2006/0143647 A1 | 6/2006 | Bill | |
| 2006/0235753 A1 | 10/2006 | Kameyama | |
| 2007/0025722 A1* | 2/2007 | Matsugu | G03B 17/16 396/263 |
| 2007/0167689 A1 | 7/2007 | Ramadas et al. | |
| 2007/0239787 A1 | 10/2007 | Cunningham et al. | |
| 2007/0255831 A1 | 11/2007 | Hayashi et al. | |
| 2007/0265507 A1* | 11/2007 | de Lemos | A61B 3/113 600/300 |
| 2007/0299964 A1 | 12/2007 | Wong et al. | |
| 2008/0059570 A1* | 3/2008 | Bill | G06Q 10/10 709/203 |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0184170 A1 | 7/2008 | Periyalwar | |
| 2008/0193031 A1* | 8/2008 | Shi | G06K 9/00899 382/250 |
| 2008/0208015 A1 | 8/2008 | Morris et al. | |
| 2008/0221472 A1 | 9/2008 | Lee et al. | |
| 2008/0267458 A1* | 10/2008 | Laganiere | G06K 9/00221 382/118 |
| 2008/0267459 A1* | 10/2008 | Nakada | G09B 19/00 382/118 |
| 2008/0287821 A1 | 11/2008 | Jung et al. | |
| 2008/0292151 A1* | 11/2008 | Kurtz | A61B 3/10 382/128 |
| 2009/0002178 A1 | 1/2009 | Guday et al. | |
| 2009/0003709 A1* | 1/2009 | Kaneda | G06K 9/4628 382/190 |
| 2009/0006206 A1 | 1/2009 | Groe et al. | |
| 2009/0083421 A1 | 3/2009 | Glommen et al. | |
| 2009/0094286 A1 | 4/2009 | Lee et al. | |
| 2009/0112694 A1 | 4/2009 | Jung et al. | |
| 2009/0112810 A1 | 4/2009 | Jung et al. | |
| 2009/0150919 A1 | 6/2009 | Lee et al. | |
| 2009/0210290 A1 | 8/2009 | Elliott et al. | |
| 2009/0217315 A1 | 8/2009 | Malik et al. | |
| 2009/0271417 A1 | 10/2009 | Toebes et al. | |
| 2009/0299840 A1 | 12/2009 | Smith | |
| 2010/0070523 A1* | 3/2010 | Delgo | G06F 17/3079 707/769 |
| 2010/0099955 A1 | 4/2010 | Thomas et al. | |
| 2010/0146052 A1* | 6/2010 | Pare | H04L 12/1822 709/204 |
| 2010/0189357 A1* | 7/2010 | Robin | G06T 11/001 382/195 |
| 2010/0259538 A1* | 10/2010 | Park | G06T 13/40 345/419 |
| 2010/0266213 A1* | 10/2010 | Hill | A61B 5/16 382/218 |
| 2010/0274847 A1 | 10/2010 | Anderson et al. | |
| 2011/0092780 A1 | 4/2011 | Zhang et al. | |
| 2011/0134026 A1 | 6/2011 | Kang et al. | |
| 2011/0143728 A1 | 6/2011 | Holopainen et al. | |
| 2011/0144971 A1* | 6/2011 | Danielson | G06F 3/011 704/1 |
| 2011/0196855 A1 | 8/2011 | Wable et al. | |
| 2011/0231240 A1 | 9/2011 | Schoen et al. | |
| 2011/0263946 A1 | 10/2011 | el Kaliouby et al. | |
| 2012/0224077 A1* | 9/2012 | Imai | H04N 1/00167 348/222.1 |
| 2012/0243751 A1* | 9/2012 | Zheng | G06K 9/6255 382/118 |
| 2012/0324491 A1 | 12/2012 | Bathiche et al. | |
| 2013/0023337 A1* | 1/2013 | Bowers | G07F 17/32 463/25 |
| 2014/0200417 A1* | 7/2014 | Senechal | G06F 19/3418 600/301 |

FOREIGN PATENT DOCUMENTS

| | | |
|---|---|---|
| KR | 10-2008-0016303 A | 2/2008 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Abiol, Alberto, et al. "Face recognition using HOG-EBGM." Pattern Recognition Letters 29.10 (2008): 1537-1543.

* cited by examiner

FACIAL ANALYSIS TO DETECT ASYMMETRIC EXPRESSIONS

RELATED APPLICATIONS

This application claims the benefit of U.S. provisional patent application "Facial Analysis to Detect Asymmetric Expressions" Ser. No. 61/703,756, filed Sep. 20, 2012. This application is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to facial analysis to detect asymmetric expressions.

BACKGROUND

The many and varied methods of human communication convey important information about individual and collective intent and desire, among myriad other emotions. The importance of automatic recognition of human emotion evidenced in speech and other forms of verbal and non-verbal communication has grown with the increasing role of speech/gesture human-computer interactions and application control. Human emotion provides a potent indicator of mood and attitude which, when considered in context, can improve customer experience in a retail setting or e-commerce application.

In addition to spoken language, humans communicate using many forms of non-verbal communication. In some forms, humans communicate by manipulating certain facial muscles, which in turn alter facial feature and form various expressions, such as smiles, frowns, and the like. Other forms of non-verbal communication include dynamic, time-varying head motions that are used to elicit many expressive head gestures, such as nodding. Isolating each such form of communication by capturing it using a sequence of images provides a richer understanding of a person's mental state. Not only do facial expressions offer robust avenues for automatic recognition of human emotion in adults, facial expressions could also prove useful for evaluating the mental states of young children who do not yet speak.

Often, the underlying feelings of people are subliminal, and not necessarily articulated, thus rendering the mood, thoughts, or mental state of a person difficult to ascertain. However, even when left unarticulated, subliminal mental states often affect how a person behaves and interacts with others on a given day. For example, an individual with a confused mental state may not be able to quickly and efficiently process information and may respond better to a slower or more repetitive explanations. Similarly, if a person had an impatient mental state, the person may respond better to a faster or terser explanation.

Additionally, analyzing the mental states of people can help to interpret individual or collective responses to surrounding stimuli. The stimuli can range from watching videos and sporting events to playing video games, interacting with websites, and observing advertisements, to name a few. Mental states run a broad gamut—from happiness to sadness, contentedness to worry, skepticism to certainty, and numerous others. These mental states are experienced either in response to the stimuli already mentioned or to everyday events: eagerness while awaiting an important telephone call, boredom while standing in line, or impatience while waiting for a cup of coffee. The Internet has only multiplied the ways in which an individual encounters stimulating information and circumstances.

Facial detection and interpretation of facial expressions under varying conditions is a task humans intuitively perform. In many cases, humans can ascertain mental state, identity, age, and gender simply by examining a person's face. The impression one receives from a person's displayed expression affects the tone and subject of interactions, conversation, and other actions. Humor and sympathy are just two examples of essential information conveyed through non-verbal facial expressions. Hence, the evaluation of mental states through facial analysis is performed by humans on a regular basis. In contrast, for computer based systems, identifying facial expressions is non-ordinary, and continues to evolve.

There are a growing number of applications which can benefit from the capability of automatically detecting human emotion. Applications for automated human emotion detection may include education, training, speech therapy, and analysis of media content to name a few.

SUMMARY

Analysis of mental states is important to assess the effectiveness of various forms of media content. In particular, mental states such as skepticism, contempt, condescension, repugnance, disgust, disbelief, cynicism, pessimism, doubt, suspicion, and distrust, are useful in assessing the effectiveness of media content such as advertising, editorials, documentaries, and the like.

These types of mental states, referred to generically as "disbelief" states, often cause an asymmetric or unilateral facial expression in a person when the person experiences such a mental state. An asymmetric facial expression is an expression in which the left and right sides of the face are considerably different. Examples include, but are not limited to, a raised eyebrow over one eye, a wink of one eye, a wince, or a smirk (an expression in which one side of the mouth is raised or lowered as compared with the other side of the mouth). The asymmetric properties of such facial expressions may be used as a basis for detecting disbelief states. When the detection of such states is performed in conjunction with subjecting a person to a stimulus—for example, an advertisement or political speech—events or dialogue from the stimulus can be correlated with a disbelief state. In this way, effectiveness of the stimulus can be assessed. A computer-implemented method for facial analysis is disclosed comprising: collecting a series of images of a face; evaluating an image from the series of images with a classifier; flipping the image to create a flipped image; evaluating the flipped image with the classifier; comparing results from the evaluating of the image and the evaluating the flipped image; and identifying an asymmetrical expression on the face based on the comparing. In embodiments, the flipping includes taking a mirror image about a y-axis. In some embodiments, the method includes detecting a fast onset and/or a fast offset of the asymmetrical expression from the series of images.

In embodiments, a computer program product embodied in a non-transitory computer readable medium for facial analysis comprises: code for collecting a series of images of a face; code for evaluating an image from the series of images with a classifier; code for flipping the image to create a flipped image; code for evaluating the flipped image with the classifier; code for comparing results from the evaluating of the image and the evaluating the flipped image; and code for identifying an asymmetrical expression on the face based on the comparing. In some embodiments, a computer system for facial analysis comprises: a memory which stores instructions; one or more processors coupled to the memory wherein the one or more processors, when executing the instructions which are stored, are configured to: collect a series of images of a face; evaluate an image from the series of images with a classifier; flip the image to create a flipped image; evaluate the flipped image with the classifier; compare results from the evaluating of the image and the evaluating the flipped image; and identify an asymmetrical expression on the face based on the comparing. Further, a computer-implemented method for facial analysis can comprise: collecting a series of images of a face; evaluating an image from the series of images; identifying an asymmetrical expression on the face in the image; and using the asymmetrical expression to evaluate a mental state.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Mental states such as skepticism, contempt, disbelief, cynicism, pessimism, doubt, suspicion, and distrust are useful to identify in analyzing the effectiveness of various media, such as advertisements and political speeches. For example, if an advertisement makes a claim that evokes doubt or suspicion in a person, then that advertisement may not produce a desired or favorable result. Advertisers, speechwriters, and the like, can use the mental state information to refine and revise their content to avoid provoking such "disbelief" mental states.

By automatically detecting mental states related to disbelief, while considering the media being observed at the time of the mental state detection, the mental states of a user can be usefully correlated to events within a piece of media content. Disbelief states may evoke asymmetric or unilateral facial expressions. An asymmetric facial expression is one in which the left and right sides of the face are considerably different. Examples include, but are not limited to, a raised eyebrow on one eye, a wink of one eye, or a smirk (an expression in which one side of the mouth is raised or lowered as compared with the other side of the mouth). By automatically detecting asymmetric or unilateral facial expressions, a person's corresponding mental state may be inferred. Temporal analysis of the facial expressions can be performed and a determination of the quickness of an asymmetric expression can be evaluated. Further, an onset time or rate for the asymmetric expression can be evaluated. Likewise, an offset time or rate for the asymmetric expression can be evaluated. Once an asymmetric expression is detected, stimuli can be analyzed to determine the cause of the asymmetric expression. In some cases a smirk or other asymmetric expression can be correlated to a video or other media that a viewer is experiencing. In some embodiments, it can be determined whether the asymmetric expression was generated in response to the media being viewed. The viewer's emotional reaction to the media can then be inferred based on the asymmetric expression. Further, the media can be rated based on the asymmetric expression.

Figure 1:
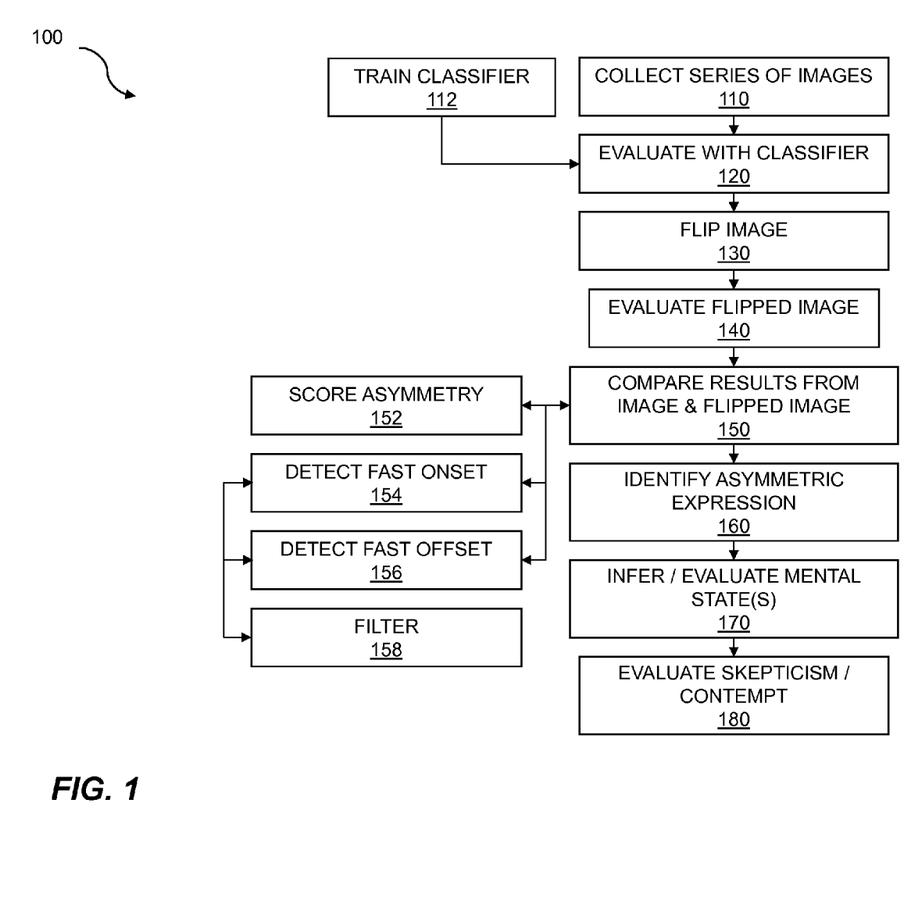
FIG. 1 is a flow diagram for asymmetric detection.

FIG. 1 is a flow diagram for asymmetric detection. The flow 100 includes a computer-implemented method for facial analysis. The flow 100 may include collecting a series of images 110 of a face. The series of images 110 may be frames from a video source. In some embodiments, the frames are consecutive frames of video. In other embodiments, frames are collected at a periodic interval—for example, every 16$^{th}$ frame may be collected. The flow 100 may include training a classifier 112 for identification of a particular facial movement or expression. Examples of classifiers include, but are not limited to, a raised eyebrow, a wink, a smirk, and a cheek puff. Training a classifier 112 can include training a support vector machine (SVM) with a Gaussian radial basis function (RBF) kernel. To train the SVM, all images from the collecting of a series of images 110 containing the right side of an asymmetric (unilateral) expression may be used as positive samples (target class) while the other images are used as negatives (non-target class). Given training samples either composed of histogram of oriented gradients (HOG) histograms $x_i$, or associated with labels $y_i$ (target or non-target), the classification function of the SVM associates a score s to the new sample x. The training of the classifier may be further based on an area under curve (AUC) analysis. This considers the area under the receiver operating characteristic (ROC) curve. The classifier may be based on one or more facial action units. The one or more facial action units may include at least one of a dimple and a lip corner pull. In some embodiments, the one or more facial action units include, but are not limited to: inner brow raiser, outer brow raiser, brow lowerer, upper lid raiser, cheek raiser, lid tightener, nose wrinkler, upper lip raiser, cheek puffer, dimpler, lip corner depressor, lower lip depressor, chin raiser, lip puckerer, lip stretcher, lip funneler, lip tightener, lip pressor, squint, and wink.

In summary, the flow 100 may include evaluating an image from the collected series of images 110 with a classifier 120. The evaluating may comprise using a classifier including, but not limited to, an eyebrow raise, a closed eye, a raised mouth corner, a lowered mouth corner, and a cheek puff. The flow 100 includes flipping the image 130 to create a flipped image. The flipping may comprise flipping the image along its vertical axis. The flow 100 may include evaluating the flipped image 140 and may comprise evaluating the flipped image with the same classifier used for the non-flipped image. The flow 100 may include comparing results 150 from the image evaluated with the classifier 120 and the evaluated flipped image 140.

The flow 100 includes identifying an asymmetrical expression 160 on the face based on the comparing. This comparing may comprise using the non-flipped trained classifier on two sets of HOG histograms, one computed from the original image x, the other one from the flipped image x̄. In embodiments, $\alpha_i$, describes a dual representation of a hyperplane's normal vector and k may be a RBF kernel function resulting from a dot product in a transformed infinite-dimensional feature space. These two sets of histograms are then input to the classifier, and the final score p predicting the likelihood of the unilateral expression (e.g. smile) is obtained by computing the absolute difference between the two outputs of the classifier as shown in the following equation:

$$p = \left| \sum_{i=1}^{m} \alpha_i(k(x_i, x) - (x_i, \bar{x})) \right|$$

In this manner, a symmetrical expression is penalized, as a perfectly symmetric face results in the minimum score of 0. Furthermore, since the classifier is trained to recognize only an asymmetric (unilateral) particular expression (e.g. a smile), it does not react to other facial asymmetry that does not pertain to the classifier.

The flipping can include taking a mirror image about a y-axis. The flow 100 may further comprise scoring asymmetry 152 based on the comparing. This may comprise computing a value for p as described previously. The scoring may provide a probability of the facial expression occurring. The flow 100 may further comprise detecting a fast onset 154 of the asymmetrical expression from the series of images. Accomplishing the detecting of a fast onset may include determining if the asymmetrical expression occurs within a predetermined time interval or number of video frames. In one embodiment, an expression is considered to have a fast onset if it occurs within 500 milliseconds. That is, if a face transitions from a baseline expression (neutral expression) to an asymmetrical (unilateral) expression within 500 milliseconds, it may be deemed a fast onset expression.

The flow 100 may further comprise detecting a fast offset 156 of the asymmetrical expression from the series of images. The detecting may comprise determining if the face reverts from an asymmetrical expression to a baseline expression within a predetermined time interval or number of video frames. In one embodiment, an expression is considered to have a fast offset if it occurs within 500 milliseconds. That is, if a face transitions from an asymmetrical (unilateral) expression to a baseline expression (neutral expression) within 500 milliseconds, it may be deemed a fast offset expression.

The flow 100 may further comprise filtering 158 of expressions based on both the fast offset and a fast onset of the asymmetrical expression from the series of images. The filtering may comprise rejecting expressions that do not qualify as fast onset and/or fast offset expressions. The flow 100 may further comprise inferring or evaluating mental states 170 based on the asymmetrical expression. The inferring can comprise associating a given expression with a corresponding mental state. The asymmetrical expression may include a smirk. In one embodiment, a smirk is associated with an expression of scorn or smugness. The asymmetrical expression may include a raised eyebrow. In one embodiment, a raised eyebrow is associated with an expression of skepticism. The asymmetrical expression may include a cheek puff. In one embodiment, a cheek puff is associated with an expression of cynicism. The asymmetrical expression may include a lowered mouth corner. In one embodiment, a lowered mouth corner is associated with an expression of disgust. The flow 100 may further comprise evaluating one of skepticism and contempt 180 based on the smirk. The asymmetrical expression may be a unilateral expression. The flow 100 may further comprise training a classifier 112 based on a receiver operating characteristic (ROC) curve, a graphical plot that illustrates the performance of a binary classifier system as its discrimination threshold is varied.

In embodiments, a frame-by-frame detector yields a confidence index on the presence of an asymmetric expression per frame. For each frame of the video, the face is extracted, cropped, and rescaled. Then, HOG features are computed on the normalized face as well as a flipped version of this face. The resulting two descriptors are input, individually, to a right hemiface trained (RHT) classifier that recognizes a right asymmetric expression. The higher the difference between the two outputs, the more likely an asymmetric expression occurs on the face. In embodiments, dynamics are evaluated to detect asymmetric events that have a clear onset and offset time. The majority of asymmetric smiles, for instance, are considered to have a short duration with a clear onset and offset. In cases where a viewer's natural facial configuration has some asymmetry around the lip region, it is unlikely that the expression is due to a reaction to media content. Based on this knowledge, the presence of an onset and offset can be used to reduce false evaluations of an asymmetric expression. The absolute difference between the two outputs of the RHT classifier, computed for each frame of the video, is used as input to the event detector is. This analysis can be used to detect and evaluate asymmetric expressions. Various steps in the flow 100 may be changed in order, repeated, omitted, or the like without departing from the disclosed inventive concepts. Various embodiments of the flow 100 may be included in a computer program product embodied in a non-transitory computer readable medium that includes code executable by one or more processors.

Figure 2:
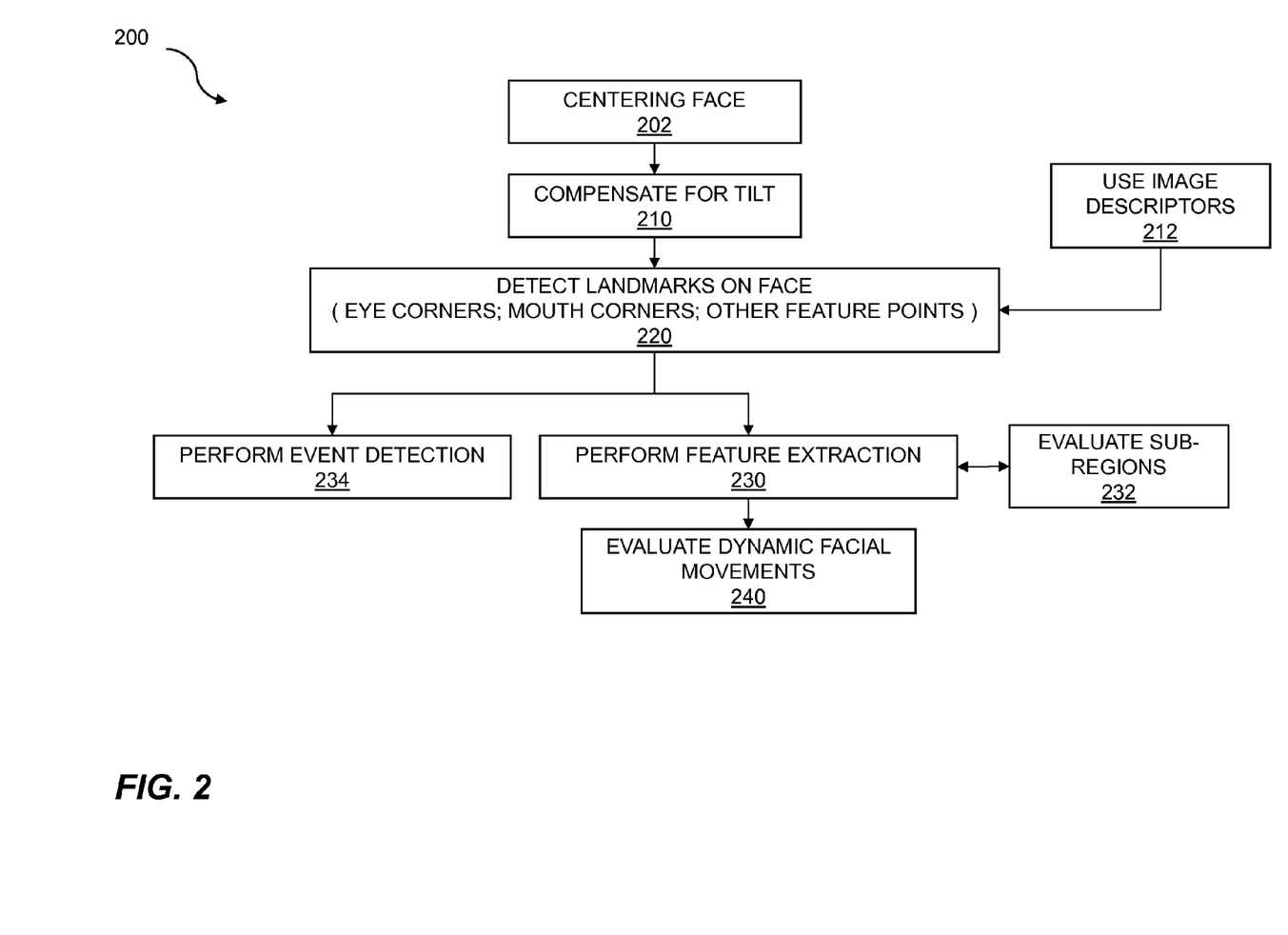
FIG. 2 is a flow diagram for facial analysis.

FIG. 2 is a flow diagram for facial analysis. The flow 200 may include centering the face 202 within an image. The flow 200 may further comprise compensating the face for a tilted head 210. The face image may be rotated such that it is in an approximately vertical orientation, with both eyes at approximately the same Y position within the image. The flow 200 may further comprise detecting landmarks on the face 220. The landmarks may include, but are not limited to, eye corners, mouth corners, eyebrows, chin, ears, and so on. The flow 200 may further comprise performing feature extraction 230 based on the landmarks which were detected. Features extracted may include, but are not limited to, an eyebrow raise, a wink, a raised mouth corner, and a lowered mouth corner. The flow 200 may further comprise evaluating a sub-region 232 of the face. A sub-region may comprise the mouth, the eyes, the eyebrows, nose, or some other portion of the face. In some embodiments, event detection 234 is performed. The flow 200 may further comprise evaluating dynamic facial movements 240. Dynamic facial movements are those that change over time; teeth-chattering or other lip or tongue motion, for example. The flow 200 may further comprise using image descriptors 212 to evaluate the image. The image descriptors may include one or more of texture, edges, and color relating to the facial expression. Various steps in the flow 200 may be changed in order, repeated, omitted, or the like without departing from the disclosed inventive concepts. Various embodiments of the flow 200 may be included in a computer program product embodied in a non-transitory computer readable medium that includes code executable by one or more processors.

Figure 3:
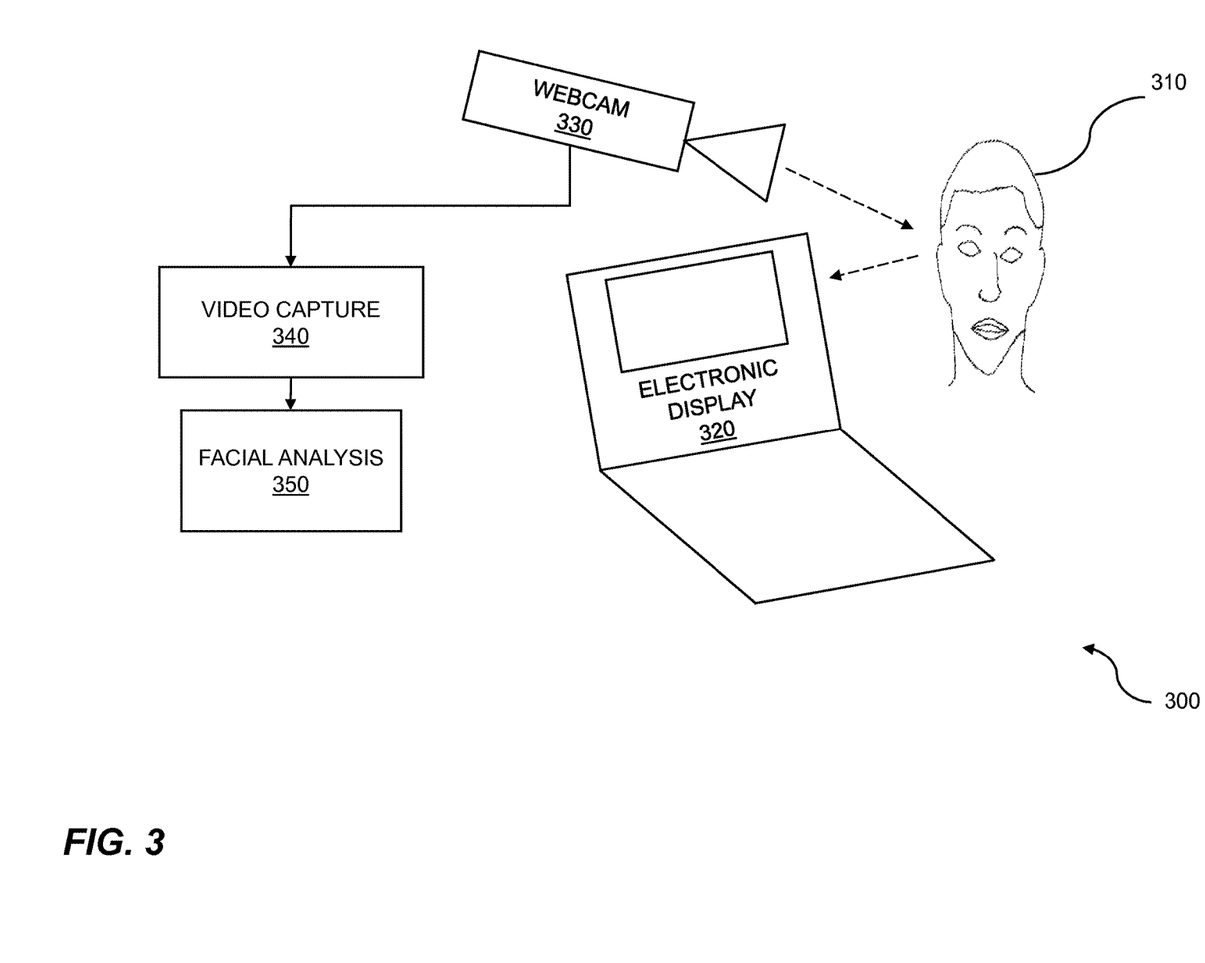
FIG. 3 is an image collection system for facial analysis.

FIG. 3 is an image collection system for facial analysis. The system 300 may include an electronic display 320 and a webcam 330. In embodiments, the system 300 captures a facial response to the electronic display 320. In other embodiments, the system 300 captures facial responses to other stimuli such as a store display, an automobile ride, a board game, or another type of experience. The captured facial data may include both video and collected information relating to mental states. In some embodiments, a webcam 330 captures video of the person 310. Images of the person 310 may also be captured by video camera, web camera still shots, a thermal imager, CCD devices, a phone camera, or another camera type apparatus. The camera apparatus may be part of a set-top box that works with a television or other display device. The camera and set-top box can be used to collect images as part of a system that evaluates facial and body motions for mental state analysis. This set-top box arrangement can enhance entertainment, communicate mental states to a social network, and so on.

The electronic display 320 may show a video or other presentation. The electronic display 320 may include a computer display, a laptop screen, a mobile device display, a cell phone display, or another electronic display. The electronic display 320 may include a keyboard, mouse, joystick, touchpad, wand, motion sensor, and other input means. The electronic display 320 may show a webpage, a website, a web-enabled application, or the like. The images of the person 310 may be captured by a video capture unit 340. In some embodiments, video of the person 310 is captured while in other embodiments a series of still images are captured. In embodiments, a webcam is used to capture the facial data.

Analysis of action units, gestures, and mental states may be accomplished using the captured images of the person 310. The action units may be used to identify smiles, frowns, and other facial indicators of mental states. The gestures, including head gestures, may indicate interest or curiosity. For example, a head motion by a person under observation toward the electronic display 320 may indicate either increased interest or a desire for clarification. Based on the captured images, analysis of physiology may be performed. This process may include individual facial analysis 350 based on the captured information and images. Further, head movement can also be evaluated and analyzed. In some embodiments, physiology is evaluated as well.

Figure 4:
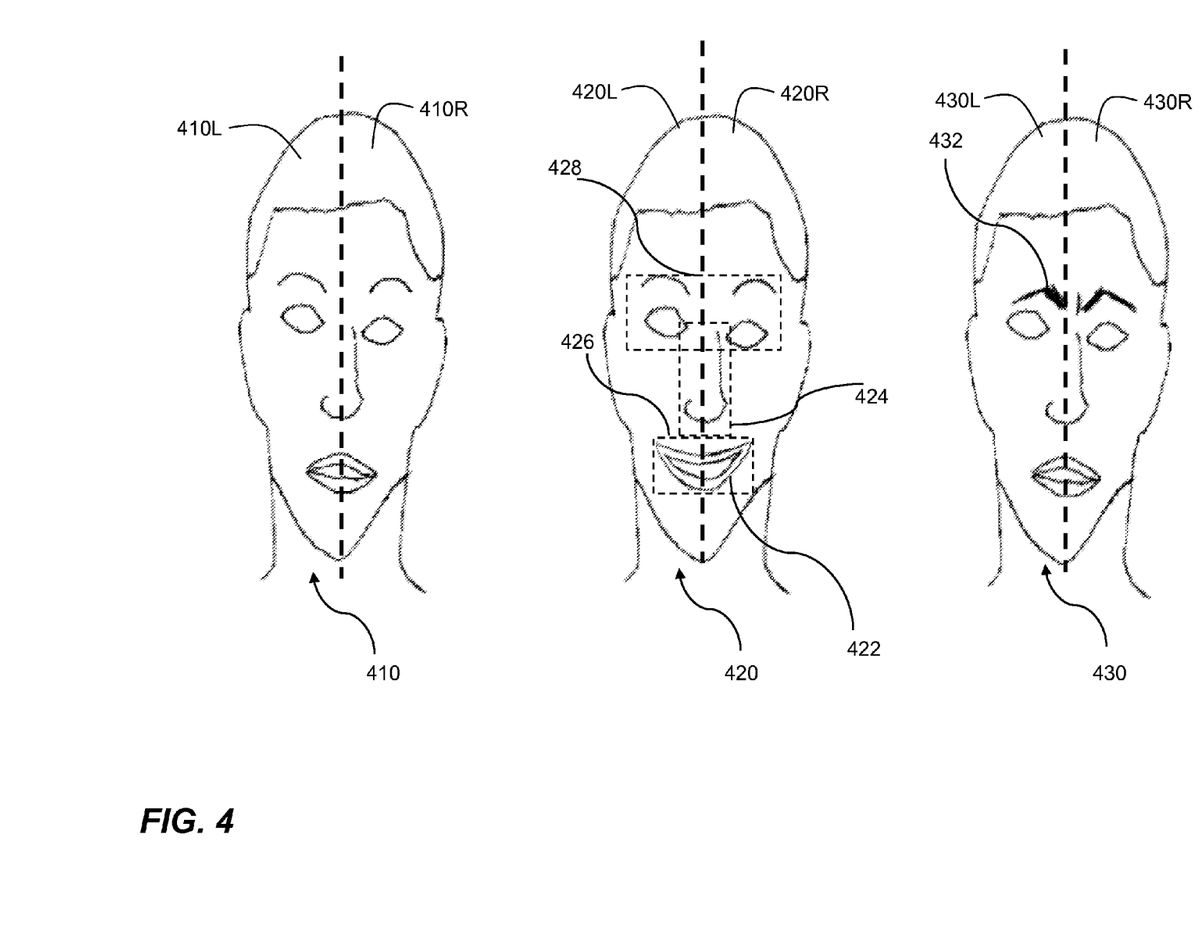
FIG. 4 is a diagram of symmetric facial expressions.

FIG. 4 is a diagram of example symmetric facial expressions. Each of these faces is similar on both the left and right side. In the embodiment shown, the example neutral face 410 does not include a smile, a frown, or another expression. In this example, the left side 410L of the face 410 is similar to the right side 410R of the face 410. The natural, symmetrical expression on the neutral face 410 as shown suggests relaxed facial muscles. An example smiling face 420 with identified sub-regions is also shown. In some embodiments, a facial sub-region is identified and extracted. In the embodiment shown, the sub-regions include a nose region 424, a mouth region 426, and an eyes region 428. A classifier may be used to evaluate one or more of the sub-regions and extract features and expressions of interest. For example, a feature such as a smile 422 can be extracted from within a sub-region; in the example shown, from within the mouth sub-region 426. For some people, their baseline facial expression may include a smile. The left side 420L of face 420 is similar to the right side 420R of face 420. An example frowning face 430 is shown with a furrowed brow 432 included. For some people, a baseline face of a furrowed brow 432 may occur. The left side 430L of face 430 is similar to the right side 430R of face 430.

Figure 5:
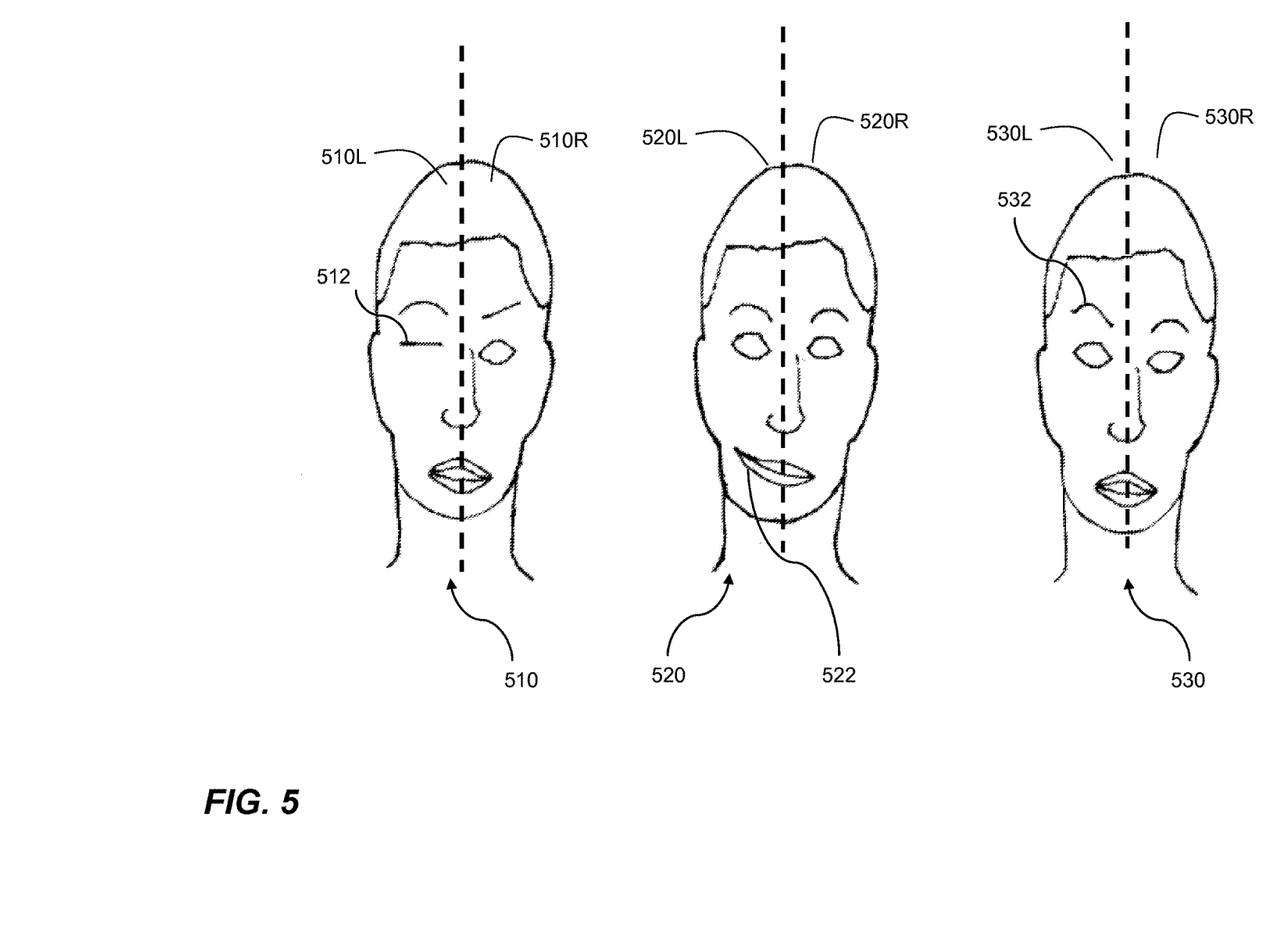
FIG. 5 is a diagram of example asymmetric facial expressions.

FIG. 5 is a diagram of example asymmetric facial expressions. The asymmetrical expressions may include a wink 512. As seen in face 510, the left side 510L of the face is different from the right side 510R of the face 510 since the left side 510L has a closed eye (wink 512) and the right side 510R has an opened eye. Hence, face 510 is asymmetrical.

The asymmetrical expression may include a smirk 522. As seen in face 520, the left side 520L of the face is different from the right side 520R of the face 520 since left side 520L has the mouth corner raised higher than on right side 520R. Hence, face 520 is asymmetrical.

The asymmetrical expression may include a single brow rise 532. As seen in face 530, the left side 530L of the face is different from the right side 530R of the face 530 since left side 530L has an eyebrow raised higher than on right side 520R. Hence, face 530 is asymmetrical. The asymmetrical expression may include a cheek puff. Other asymmetrical expressions may include a lowered lip corner, a tongue extended from the mouth on one side, and so on. The asymmetrical expression may be evaluated based on the deviation each expression evidences when compared to a neutral face that has been previously evaluated.

Figure 6:
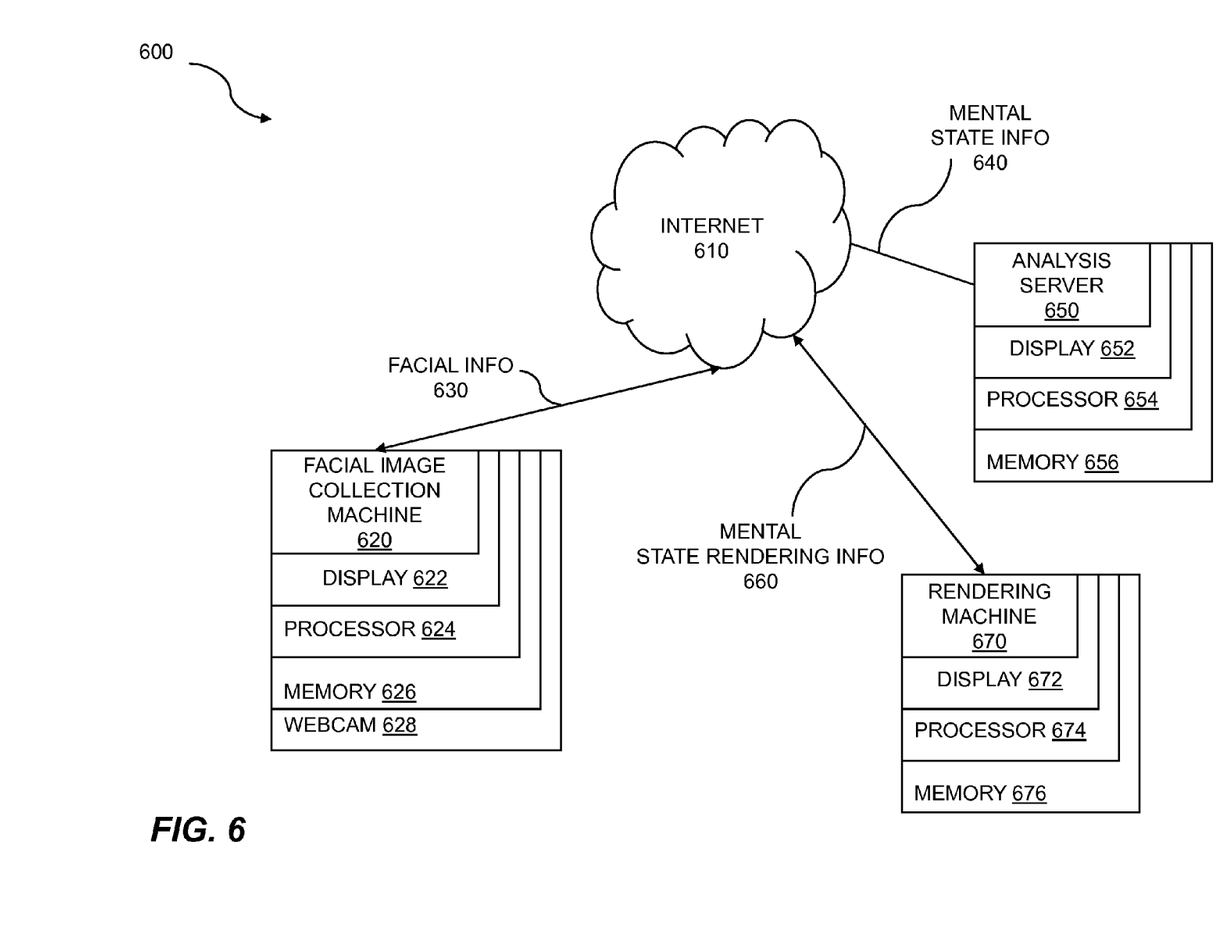
FIG. 6 is a system diagram for performing mental state analysis.

FIG. 6 is a system diagram for performing facial analysis to detect asymmetric expressions. In embodiments, the computer system for performing facial analysis to detect asymmetric expressions comprises a facial image collection machine 620 configured to collect a series of images of a face. The facial image collection machine may comprise one or more processors 624 coupled to a display 622; a memory 626 designed to store facial image data, instructions, and the like; and a webcam 628. The display 622 may be any electronic display, including but not limited to, a computer display, a laptop screen, a net-book screen, a tablet computer screen, a cell phone display, a mobile device display, a remote with a display, a television, a projector, or the like. The webcam 628, as the term is used herein, may refer to a video camera, a still camera, a thermal imager, a CCD device, a phone camera, a three-dimensional camera, a depth camera, multiple webcams used to show different views of a person, or any other type of image capture apparatus that may allow data captured to be used in an electronic system. The facial image collection machine may be configured to transmit facial information 630 to a server via the Internet 610 or other network. The display and the camera may be coupled to a set-top box type device.

An analysis server 650 may obtain mental state information 640 from the internet. The analysis server 650 may comprise one or more processors 654 coupled to a display 652 and a memory 656 designed to store system information, instructions, and the like. The display 652 may be any electronic display, including but not limited to, a computer display, a laptop screen, a net-book screen, a tablet computer screen, a cell phone display, a mobile device display, a remote with a display, a television, a projector, or the like. The one or more processors 654, when executing the instructions which are stored, may be configured to take an image from the series of images and use a classifier to evaluate the image as well as a flipped version of that image. In some embodiments, the rendering of emotional status can occur on a different computer than the client machine 620 or the analysis server 650. This computer may be a rendering machine 670 which receives facial information 630, mental state information 640 from the analysis machine 650, or both and may be considered mental state rendering information 660. In embodiments, the rendering machine 670 includes one or more processors 674 coupled to a memory 676, and a display 672. The rendering may include generation and display of emoticons. Smiley, wink, and other emoticons can be generated and shown. In some embodiments, the emoticons can be can be communicated across a social network in part of an effort to mental states. In at least one embodiment, the facial image collection machine function, the analysis server function, and/or the rendering machine function are performed by one machine. The system 600 may include a computer program product comprising code for collecting a series of images of a face, code for evaluating an image from the series of images with a classifier, code for flipping the image to create a flipped image, code for evaluating the flipped image with the classifier, code for comparing results from the evaluating of the image and the evaluating the flipped image, and code for identifying an asymmetrical expression on the face based on the comparing.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for facial analysis comprising:
   collecting a series of images of a face;
   evaluating an image from the series of images with a classifier; flipping the image to create a flipped image; evaluating the flipped image with the classifier;
   comparing results from the evaluating of the image and the evaluating the flipped image; identifying an asymmetrical expression on the face based on the comparing; inferring mental states based on the asymmetrical expression wherein the mental states include a mental state of disbelief; and
   scoring the asymmetrical expression based on the comparing, wherein the left and right sides of the face are different, and wherein the scoring provides a probability of a facial expression occurring, wherein the scoring includes:
   providing a histogram computed from the image to a classifier to produce a first output; providing a histogram computed from the flipped image to a classifier to produce a second output: and computing a difference between the first output and the second output by subtracting the second output from the first output.

2. The method of claim 1 wherein the flipping includes taking a mirror image about a y-axis.

3. The method of claim 1 further comprising centering the face within the image.

4. The method of claim 1 further comprising compensating the face for a tilted head.

5. The method of claim 1 further comprising detecting a fast onset of the asymmetrical expression from the series of images.

6. The method of claim 1 further comprising detecting a fast offset of the asymmetrical expression from the series of images.

7. The method of claim 6 further comprising filtering based on both the fast offset and a fast onset of the asymmetrical expression from the series of images.

8. The method of claim 1 wherein the asymmetrical expression includes a smirk.

9. The method of claim 8 further comprising evaluating skepticism or contempt based on the smirk.

10. The method of claim 1 wherein the asymmetrical expression includes a wink.

11. The method of claim 1 wherein the asymmetrical expression includes a single brow rise.

12. The method of claim 1 wherein the asymmetrical expression includes a cheek puff.

13. The method of claim 1 wherein the asymmetrical expression is a unilateral expression.

14. The method of claim 1 wherein the series of images are from a video.

15. The method of claim 14 wherein the video is captured with a webcam.

16. The method of claim 1 further comprising training the classifier based on a receiver operating characteristic (ROC) curve.

17. The method of claim 16 wherein the training the classifier is further based on an area under curve (AUC) analysis.

18. The method of claim 1 wherein the classifier is based on one or more facial action units.

19. The method of claim 18 wherein the one or more facial action units includes a dimpler or a lip corner pull.

20. The method of claim 1 further comprising evaluating dynamic facial movements.

21. The method of claim 1 further comprising evaluating a sub-region of the face.

22. The method of claim 21 wherein the sub-region includes mouth or eyes.

23. The method of claim 1 further comprising using image descriptors to evaluate the image.

24. The method of claim 23 wherein the image descriptors include one or more of texture, edges, and color relating to a facial expression.

25. The method of claim 1 further comprising detecting landmarks on the face.

26. The method of claim 25 further comprising performing feature extraction based on the landmarks which were detected.

27. The method of claim 26 wherein the landmarks on the face include one or more from a group including eye corners, mouth corners, and eyebrows.

28. The method of claim 1 wherein the mental state of disbelief includes skepticism, contempt, condescension, repugnance, disgust, disbelief, cynicism, pessimism, doubt, suspicion, or distrust.

29. The method of claim 1 wherein the scoring includes:
   providing a second histogram computed from the image to a classifier to produce a third output;
   providing a second histogram computed from the flipped image to a classifier to produce a fourth output; and
   computing a difference between the third output and the fourth output by subtracting the fourth output from the third output.

30. The method of claim 29 wherein the scoring includes determining a summation of differences by summing:
   the difference between the first output and the second output; and
   the difference between the third output and the fourth output.

31. The method of claim 30 wherein the scoring includes determining a likelihood of unilateral expression by determining the absolute value of the summation of differences.

32. The method of claim 1 wherein the histograms comprise histogram of oriented gradients (HOG) analysis.

33. A computer program product embodied in a non-transitory computer readable medium for facial analysis, the computer program product comprising code which causes one or more processors to perform operations of:
   collecting a series of images of a face;
   evaluating an image from the series of images with a classifier; flipping the image to create a flipped image; evaluating the flipped image with the classifier;
   comparing results from the evaluating of the image and the evaluating the flipped image;
   identifying an asymmetrical expression on the face based on the comparing;

inferring mental states based on the asymmetrical expression wherein the mental states include a mental state of disbelief; and scoring the asymmetrical expression based on the comparing, wherein the left and right sides of the face are different, and wherein the scoring provides a probability of a facial expression occurring, wherein the scoring includes:

providing a histogram computed from the image to a classifier to produce a first output;

providing a histogram computed from the flipped image to a classifier to produce a second output; and computing a difference between the first output and the second output by subtracting the second output from the first output.

34. A computer system for facial analysis comprising: a memory which stores instructions;

one or more processors coupled to the memory wherein the one or more processors, when executing the instructions which are stored, are configured to: collect a series of images of a face;

evaluate an image from the series of images with a classifier; flip the image to create a flipped image; evaluate the flipped image with the classifier;

compare results from the evaluating of the image and the evaluating the flipped image;

identify an asymmetrical expression on the face based on the comparing; infer mental states based on the asymmetrical expression wherein the mental states include a mental state of disbelief; and score the asymmetrical expression based on the comparing, wherein the left and right sides of the face are different, and wherein the scoring provides a probability of a facial expression occurring, wherein the scoring includes:

providing a histogram computed from the image to a classifier to produce a first output:

providing a histogram computed from the flipped image to a classifier to produce a second output: and compute a difference between the first output and the second output by subtracting the second output from the first output.

35. A computer-implemented method for facial analysis comprising:

collecting a series of images of a face; evaluating an image from the series of images; identifying an asymmetrical expression on the face in the image; scoring the asymmetrical expression, wherein the left and right sides of the face are different, and wherein the scoring provides a probability of a facial expression occurring, wherein the scoring includes:

providing a histogram computed from the image to a classifier to produce a first output:

providing a histogram computed from a flipped image to a classifier to produce a second output: and computing a difference between the first output and the second output by subtracting the second output from the first output: and using the asymmetrical expression and score to evaluate a mental state wherein the mental state includes a mental state of disbelief.

* * * * *